United States Patent [19]

Ellwood et al.

[11] 4,248,862

[45] Feb. 3, 1981

[54] IMMUNOGENIC CELL ENVELOPE PREPARATIONS

[75] Inventors: Derek C. Ellwood; Richard J. Manchee; Andrew Robinson, all of Salisbury, England

[73] Assignee: The Secretary of State in Her Britannic Majesty's Government of the United Kingdom of Great Britain and Northern Ireland, London, England

[21] Appl. No.: 12,857

[22] Filed: Feb. 16, 1979

[30] Foreign Application Priority Data

Feb. 17, 1978 [GB] United Kingdom ............... 6462/78

[51] Int. Cl.³ .............................................. A61K 39/10
[52] U.S. Cl. .................................................. 424/92
[58] Field of Search ........................................ 424/92

[56] References Cited

U.S. PATENT DOCUMENTS

| | | | |
|---|---|---|---|
| 2,965,543 | 12/1960 | Thiele | 424/92 |
| 3,141,824 | 7/1964 | Dahlstrom | 424/92 |
| 3,395,219 | 7/1968 | Millman | 424/22 |

FOREIGN PATENT DOCUMENTS

| | | | |
|---|---|---|---|
| 2461439 | 1/1976 | Fed. Rep. of Germany | 424/92 |
| 2356429 | 1/1978 | France | 424/92 |
| 41-11357 | 6/1966 | Japan | 424/92 |

OTHER PUBLICATIONS

Robinson, A. et al., FEMS Microbiol. Lett (1979) 5(3): 131-134, Solubilization of the Protective Antigens of Bordetella pertussis', CA. 90#174558M (1979).
Dyke et al., J. Med. Virol., 1978, 2(2): 143-152 Glycoproteins of Representative Paramyxoviruses Isolation and Antigenic Analysis Using a Zwitterionic Surfactant, CA. 89#102953T (1978).
Gow et al. Microbios. (1976):15(61-62):209-219, Radiolabeling of Bordetella pertussis Envelope Proteins by $^{125}$I-Lactoperoxidase, CA. 86#52631b (1977).
Parton et al., CA. 834600g, 1975 of J. Med Microbiol, 1975, 8(1):47-57, Cell Envelope Proteins of Bordetella pertussis.
Wardlaw et al., CA. 85 2260p (1976) of J. Med. Microbiol. 1976 9(1):89-100 Loss of . . . Envelope Polypeptides in Cultural Variants of Bordetella pertussis.
Allen et al., FEBS Letters 57(2):158-162, Sep. 1975, The Use of Zwitterionic Surfactants in the Agarose Chromatography of Biological Membranes.

*Primary Examiner*—Shep K. Rose
*Attorney, Agent, or Firm*—Stevens, Davis, Miller & Mosher

[57] ABSTRACT

An antigenically-active cell envelope fraction from bacterial cells, especially *Bordetella pertussis*, may be isolated by disrupting the cells, separating the cell envelopes from the other cell components, extracting the separated envelopes with a solution of a zwitterionic surfactant and precipitating the cell envelope preparation from the resulting extract by the addition of a lower alkyl ($C_1$ to $C_5$) alcohol, preferably ethanol. The preferred extractant is an N, N, N-trialkyl zwitterionic compound especially an N, N, N-trialkyl-α-amino acid or an N, N, N-trialkyl amine oxide.

The cell envelope fraction obtained from *B. pertussis* is highly protective against whole bacteria when tested by standard vaccine mouse potency assay and has a greatly reduced lipopolysaccharide content compared with either whole cells or crude cell envelopes, greatly reducing the risk of undesirable side-effects from vaccination.

12 Claims, No Drawings

IMMUNOGENIC CELL ENVELOPE PREPARATIONS

The invention relates to the production of cell envelope preparations having immunogenic properties and potentially useable as vaccines. It is especially concerned with the production of such preparations from bacteria of the genus Bordetella, particularly the species *Bordetella pertussis*.

It is known that the outer layers (commonly termed the envelopes) of certain bacterial cells, including the species *Bordetella pertussis*, have antigenic properties and are protective when used as vaccines. However, many techniques of cell envelope isolation and fractionation are non-specific, destroy the protective activity or produce low yields of active material. There is thus a need for selective extraction methods producing a high yield of active material with the minimum of non-immunogenic cell components.

According to the present invention, a process for producing an antigenically-active cell envelope preparation from bacterial cells comprises disrupting the cells, separating the cell envelopes from the other cell components, extracting the separated envelopes with a solution of a zwitterionic surfactant and precipitating the cell envelope preparation from the resulting extract. Preferably the extractant is an N,N,N-trialkyl zwitterionic compound, especially an N,N,N-trialkyl-α-amino acid, particularly an N,N,N-trialkyl glycine or an N,N,N-trialkyl amine oxide. More particularly, N-alkyl-N,N-dimethyl-glycine or N-alkyl-N,N-dimethyl amine oxides, for example those sold under the trade names Empigen BB (a lauryl/myristyl dimethyl glycine), OB (a lauryl/myristyl dimethyl amine oxide) or are preferred.

Zwitterionic surfactants are preferred to other classes of surfactants such as ionic and uncharged surfactants, since they appear able to selectively extract high yields of antigenically-active material from the bacterial cells. By comparison ionic surfactants in which the charged species are separable, such as sodium dodecyl sulphate, are found to extract high yields of a protective material that is low in antigenic-activity, (this is presumably due to the denaturation of the protective components in the extract by the ionic surfactant). On the other hand, uncharged surfactants, such as Triton X-100, (Trade Mark), though not denaturing the protective components found in the extract, fail to extract sufficient quantities of the antigenically-active material.

It appears, though the invention is not limited in any way by this explanation, that the zwitterionic surfactants resemble the ionic surfactants in their ability to extract sufficient protective material from the bacterial cells and the uncharged surfactants in their ability to retain antigenic activity.

The process of the invention may be applicable to any strain producing an antigenically-active envelope, for example bacteria of the genus Bordetella, especially the species *Bordetella pertussis*. Suitable strains include the isolate designated M2 available from Dr. N. W. Preston, Department of Bacteriology & Virology, University of Manchester and the 'Tohama' strain available from the Japanese Federation of Culture Collections of Microorganisms, and strain 134 available from Prof. A. Wardlaw Dept. of Microbiology Anderson College 58 Dumbarton Rd, Glasgow G11 6NU. However, the strain used does not appear to be critical and other strains may be used.

The cells may be produced by any conventional method, but are preferably cells which have been cultured in a liquid medium for not more than 36 hours since these generally produce cell envelope preparations with higher protective activity than those from longer term cultures. The cells are preferably disrupted by conventional mechanical techniques. Other techniques such as sonification or chemical disruption may be suitable in some cases, but are liable to cause undesirable changes in the cell envelope.

The extraction solution should normally contain between about 0.1% to 5%, especially 0.5% to 5% (v/v) of the surfactant. Preferably the surfactant concentration is 0.5% to 1.5%, typically about 0.6% (v/v) of the surfactant. It should normally have a pH of less than 9 and preferably 7.5 to 8.5 and this is preferably achieved by use of a phosphate buffer. Other buffers may be suitable, but some, for example tris-HCL may reduce the activity of the product. The extraction period should be controlled to achieve maximum specificity of extraction and should, for example, preferably be no more than 90 minutes at 37° C. The undissolved cell envelope material may be removed by centrifugation. The immunogenic component of the cell envelope extract may be precipitated from the extract for example by the addition of a lower alkyl ($C_1$ to $C_5$) alcohol, preferably ethanol, and may be dispersed in water and formulated into a vaccine in a conventional manner. Removal of any remaining surfactant from the precipitated material or original extract may be achieved by pressure dialysis against water or other conventional techniques.

The antigenically-active cell envelope preparation produced by extraction of cell walls with a zwitterionic surfactant in accordance with the present invention is a very much purer antigen preparation than either the original cells or the crude cell walls and hence may be expected to yield a vaccine less liable to produce side effects. However the preparation is still a mixture of proteins and hence may be susceptible to further separation to yield one or more antigen preparations. Hence the preparation prepared by the process of the present invention may be useful either as a vaccine in its own right or as an intermediate in the production of a vaccine. When used as a vaccine in its own right, the dosage rate should typically be within the range 2.5 to 250 μg. per kg body weight. The vaccine may be used alone or with adjuvants and by single or multiple innoculation in accordance with conventional practices.

Specific embodiments of the process of the invention will now be described by way of example.

EXAMPLE 1

Cells of *Bordetella pertussis* strain M2 were grown for 24 hours at 37° C. in an aerated liquid medium as described by Cohen & Wheeler, American Journal of Public Health, Vol. 36 (1946) pp 371–376.

The cells were disrupted by disintegration in a MSK Braun homogeniser for 4 minutes at 5° C. The cell envelopes were separated by differential centrifugation employing 2 washes of the envelopes in 0.9% (w/v) sodium chloride and 2 washes in distilled water. The product was sterilised and freed from heat labile toxin by heating in an aqueous suspension to 56° C. for 30 minutes.

The separated envelopes were shaken at a protein concentration of 5 mg/ml for 90 minutes at 37° C. in an aqueous solution of 0.6% (v/v) of an N-alkyl N,N-dimethyl glycine (alkyl group predominantly lauryl/myristyl) (supplied by Marchon Division, Albright and Wilson Ltd under the Trade Mark Empigen BB) in a 0.05 M sodium phosphate buffer (pH 8.0). The extract was separated by centrifugation and treated dropwise at 4° C. with 40% of its own volume of ethanol. The precipitated material was collected by centrifugation and dispersed in distilled water. Traces of surfactant were removed by further centrifugation followed by redispersal in distilled water. The traces of surfactant could also be removed by pressure dialysis against water.

The purified material was tested as a suspension in distilled water for protective activity by the vaccine mouse potency assay as recommended by Kendrick, Eldering, Dixon & Misner, American Journal of Public Health Vol. 37 (1947) pp 803–810 and found to be highly protective. The ethanol precipitate had a reduced lipopolysaccharide content compared with the soluble Empigen BB extract. The lipopolysaccharide content can be further reduced by column chromatography or other well known means.

EXAMPLE 2

The process of Example 1 was repeated on cells of *Bordetella pertussis* strain 134. The purified material was tested by the vaccine mouse potency assay and found to be highly protective.

EXAMPLE 3

The process of Example 1 was repeated on cells of *Bordetella pertussis* 'Tohama' strain to produce purified antigenic material.

We claim:

1. In a process for producing an antigenically-active cell envelope preparation from bacterial cells of the species *Bordetella pertussis* comprising disrupting the cells, separating the resulting cell envelopes from the other cell components, extracting the separated envelopes with a surfactant extraction solution and precipitating the cell envelope preparation from the resulting extract, the improvement which comprises extracting the said separated envelopes with a solution containing a zwitterionic surfactant selected from the group consisting of an N,N,N-trialkyl glycine and an N,N,N-trialkyl amine oxide.

2. A process according to claim 1 wherein the zwitterionic surfactant is selected from a group consisting of N-alkyl-N,N-dimethyl glycine derivatives and N-alkyl-N,N-dimethyl amine oxides.

3. A process according to claim 1 wherein the extraction solution contains between 0.1% and 5% (v/v) of the zwitterionic surfactant.

4. A process according to claim 3 wherein the extraction solution contains between 0.5% and 5% (v/v) of the zwitterionic surfactant.

5. A process according to claim 4 wherein the extraction solution contains between 0.5% and 1.5% (v/v) of the zwitterionic surfactant.

6. A process according to claim 5 wherein the extraction solution contains about 0.6% (v/v) of the zwitterionic surfactant.

7. A process according to claim 1 wherein the extraction solution is buffered to a pH of less than 9.

8. A process according to claim 7 wherein the extraction solution is buffered to a pH between 7.5 and 8.5.

9. A process according to claim 1 wherein the extraction period is not more than 90 minutes at 37° C.

10. A process according to claim 1 wherein the said cell envelope preparation is precipitated by the addition of a lower alkyl alcohol.

11. A process according to claim 10 wherein the lower alkyl alcohol is ethanol.

12. A process according to claim 1 wherein the bacterial cells have been cultured in liquid medium for no more than 36 hours at 37° C.

* * * * *

UNITED STATES PATENT AND TRADEMARK OFFICE
CERTIFICATE OF CORRECTION

PATENT NO. : 4,248,862
DATED : February 3, 1981
INVENTOR(S) : Derek Clifford Ellwood et al.

It is certified that error appears in the above-identified patent and that said Letters Patent are hereby corrected as shown below:

On the face of the patent, the Assignee should read as follows:

---The Secretary of State for Social Services in Her Britannic Majesty's Government of the United Kingdom of Great Britain and Northern Ireland, London, England---

Signed and Sealed this

Second Day of June 1981

[SEAL]

Attest:

RENE D. TEGTMEYER

*Attesting Officer*    *Acting Commissioner of Patents and Trademarks*